(12) United States Patent
Dillard

(10) Patent No.: US 11,135,083 B2
(45) Date of Patent: Oct. 5, 2021

(54) BARBED NASAL IMPLANT AND METHOD FOR ADJUSTABLE REPAIR AND RE-POSITIONING OF THE NASAL VALVE LIGAMENT

(71) Applicant: David G. Dillard, Atlanta, GA (US)

(72) Inventor: David G. Dillard, Atlanta, GA (US)

( * ) Notice: Subject to any disclaimer, the term of this patent is extended or adjusted under 35 U.S.C. 154(b) by 133 days.

(21) Appl. No.: 16/698,504

(22) Filed: Nov. 27, 2019

(65) Prior Publication Data

US 2020/0170823 A1 Jun. 4, 2020

Related U.S. Application Data

(60) Provisional application No. 62/773,723, filed on Nov. 30, 2018.

(51) Int. Cl.
*A61F 5/08* (2006.01)
*A61B 17/06* (2006.01)

(52) U.S. Cl.
CPC ....................................... *A61F 5/08* (2013.01)

(58) Field of Classification Search
CPC .. A61F 2/186; A61F 5/08; A61B 2017/06176; A61B 17/06166; A61B 17/24
See application file for complete search history.

(56) References Cited

U.S. PATENT DOCUMENTS

2011/0251634 A1* 10/2011 Gonzales ............. A61B 17/064
606/199

* cited by examiner

*Primary Examiner* — Majid Jamialahmadi
(74) *Attorney, Agent, or Firm* — Morris, Manning & Martin, LLP; John R. Harris

(57) ABSTRACT

A method and device for non-surgically repairing and augmenting internal nasal valve ligaments of a patient. The method and device comprise tunneling a working device subcutaneously into the ligaments of the nasal valve and the surrounding soft tissues and periosteum of the adjacent bony structures, causing a tightening of the nasal valve ligaments and repositioning the nasal valve in adjustable fashion. A device comprising a barbed elongate implant is introduced by tunneling subcutaneously into the nasal valve ligament allowing for structural re-positioning of the nasal valve cartilage structures and tightening of the ligaments, which is adjustable intra-operatively and allows for structural support of the nose and/or causes a change in the external shape of the nose.

11 Claims, 10 Drawing Sheets

BARBED NASAL IMPLANT AND METHOD FOR ADJUSTABLE REPAIR AND RE-POSITIONING OF THE NASAL VALVE LIGAMENT

CROSS-REFERENCE TO RELATED APPLICATIONS

This application claims benefit under 35 U.S.C. § 119(e) of U.S. Provisional Patent Application No. 62/773,723 filed Nov. 30, 2018, entitled "BARBED NASAL IMPLANT AND METHOD FOR ADJUSTABLE REPAIR AND RE-POSITIONING OF THE NASAL VALVE LIGAMENT", which is incorporated herein by reference as set forth herein in its entirety.

STATEMENT REGARDING FEDERALLY SPONSORED RESEARCH OR DEVELOPMENT

Not applicable.

BACKGROUND

The information provided below is not admitted to be prior art the present invention, but is provided solely to assist the understanding of the reader.

The nose functions to regulate airflow and humidify the air which we breathe. The nasal valve represents the soft segment of the nose, which is supported by cartilage, muscle, and ligament, and which generally is the portion of the soft external nose adjacent to the central bony opening of the facial bones. This opening is also known as the piriform aperture. The septum, which is the cartilage and bone supported midline wall of the nose, along with the nasal bones formed the central support for two pairs of leaf spring and C-spring shaped cartilage is known as the upper and lower lateral cartilages respectively. The upper and lower lateral cartilage structures along with a series of smaller cartilage structures provide support for the lateral nasal walls known as the alae. Muscular attachments between the cartilages of the lower external nose and between the bones of the face and the cartilages abutting those bones allows for adjustment of the resistance through the nose. Deficient ligamentous attachments for the cartilage structures results in the soft lateral walls of the nose being sucked into the airflow causing increased resistance on inspiration. Internal nasal valve collapse can be a consequence of previous surgery, trauma, aging, or primary weakness of the attachments with the lower and upper lateral cartilages or the upper and lower lateral cartilages themselves.

Further description of the nasal valve and its functions can be found in the article by Cole, "The Four Components of the Nasal Valve", American Journal of Rhinology, Vol. 17, No. 2, pages 107 through 110 (2003).

Importance of repairing the nasal valve is emphasized by Rhee et al., "Nasal Valve Surgery Improves Disease-Specific Quality of Life", Laryngoscope, Vol. 115, pages 437 to 440 (2005), who noted significant improvements and quality-of-life scores for patients treated for nasal valve collapse. Multiple different techniques for repair of the nasal valve have included alar batten grafting, spreader grafts, and placement of synthetic support materials which require open surgical techniques. Techniques for supporting the ligament is structures have included percutaneous suture fixation and Weir excision technique (the latter dating to the early part of the 20th century. Karen et al., "The Use of Percutaneous Sutures for Graft Fixation in Rhinoplasty", archives Facial Plastic Surgery, Vol. 5, pages 193 to 196 (2003) and Friedman M, Ibrahim H, Syed Z, "Nasal Valve Suspension: An Improved, Simplified Technique for Nasal Valve Collapse", Laryngoscope 2003; 0.113(2):381-385 are two articles which describe support of the lateral nasal wall using suture technique. Other techniques include thermal and radio frequency ablation techniques for the soft tissues of the nasal valve and nasal ligaments. Disadvantages of the above named techniques include the requirement for open surgical techniques or the inability to adjust the tissues precisely while the patient is able to breathe in during spontaneous respirations. Breathing in during spontaneous respirations allows for evaluation of the sufficiency of the repair technique for the ligaments.

External (non-implanted) nasal dilators are placed and removed by the patient such as the Breathe Right® strips (e.g. U.S. Pat. Nos. 5,533,499 and 6,318,362) have a disadvantage of being uncomfortable, readily visible, and easily displaced.

There is, therefore, a need for a minimally invasive, non-surgical device and methods for repair of the nasal valve ligaments which is adjustable during the procedure. Unlike previous implant methods, the current device and method focuses on a tunneling device and a barbed implant which allow for compression of the ligament along with gradual adjustment during the procedure. According to one aspect, use of certain dissolvable or absorbable materials for the implant results in eventual replacement of the implant material by the inflammatory response, causing removal of the implant and deposition of connective and elastic tissue. Preferably, the desired technique does not require surgical incisions.

FIELD OF THE INVENTION

Aspects of the present invention relate to methods, implants, and devices for nonsurgically repairing the nasal ligaments, and non-surgically supporting nasal function including nasal valve function and cosmetic changes to the shape of the nose. The device is introduced through a tiny incision with the aid of a tunneling device into the nasal ligaments and tissues, and by specially designed implant, which allows for intraoperative adjustment of the structures.

BRIEF SUMMARY

According to one aspect, an object of the present invention includes providing a device and method and system for repairing deficient nasal valve cartilage ligamentous support. Lack of ligamentous support is a primary contributor to age-related nasal valve collapse, as well as primary nasal valve collapse.

Briefly described, a method and device are disclosed for non-surgically repairing and augmenting internal nasal valve ligaments of a patient. The method and device comprise tunneling a working device such as a hypodermic needle subcutaneously into the ligaments of the nasal valve and the surrounding soft tissues and periosteum of the adjacent bony structures, causing a tightening of the nasal valve ligaments and repositioning the nasal valve in adjustable fashion. A device comprising a barbed elongate implant is introduced by tunneling subcutaneously into the nasal valve ligament allowing for structural re-positioning of the nasal valve cartilage structures and tightening of the ligaments, which is adjustable intra-operatively and allows for structural support of the nose and/or causes a change in the external shape of the nose.

According to one aspect, the desirable effect of opening the nasal passage and expanding the nasal valve ligament is achieved nonsurgically by compressing the ligaments via a minimally invasive technique. Treatment of the nasal ligaments include injecting a barbed working implant into the tissues of the nasal ligament. This effects tightening by compressing the ligament between oppositely oriented barbs on the implant and by employing a biologically compatible material which, in one aspect, gradually dissolves and is replaced by elastic and fibrous tissues resulting from the inflammatory response. The implant can be utilized to strengthen the ligaments between the lower and upper lateral cartilages and the surrounding nasal bones. The implant can also be used to strengthen the attachments of ligaments between the right and left upper and lower lateral cartilages across the midline. Further, the lower lateral cartilages are attached to the cartilage portion of the nasal septum and this ligament can be strengthened with the implant thus allowing for tightening of the lateral nasal wall along a third vector. Finally, application of this method and device along the ligament between the upper lateral cartilages and septum and nasal bones helps lift cartilage and soft tissue out of the airway.

Another aspect of the disclosed method and device involves a biodegradable material such as polydiaxanone (abbreviated PDO) with barbs attached to and angled more or less acutely away from the central suture material which comprises a continuous thread or cord-like structure. Suitable materials include those typically used as surgical sutures, generally classified as either absorbable or non-absorbable depending on whether the body will naturally degrade and absorb the suture material over time. Absorbable suture materials suitable for use may also include synthetics such as polyglycolic acid, polylactic acid, and caprolactone.

According to one aspect, the barbs can be paired or staggered. The orientation of the barbs is such that an anchor point (such as the midpoint of the implant material or another advantageous position along the central implant) is surrounded with oppositely oriented barbs. There may be more than one anchor point but the wider aspect of the paired or staggered barbs is closer to the "anchor point" than the more narrow attachment to the central implant. The barbs are preferably of sufficient stiffness and length to dig into and retain the surrounding soft tissue of the nasal ligaments. The barbs can be created by any variety of manufacturing techniques such as molding barbs onto the material of the implant. In another embodiment, the barbs can be created cutting, notching, ablating, or otherwise removing the central material of the implant to achieve the desired barbs.

According to another aspect, the barbed implant is placed utilizing a blunt tipped hollow needle similar to a hypodermic needle placed though a pilot hole created in the skin by a narrow cutting device such as a large gauge hypodermic needle or narrow tipped scalpel. The method further comprises steps of placing the implant across the desired ligament and detaching it from the delivery device with a portion of the barbed implant extending beyond the skin. The implant is then grasped to provide counter tension as the soft tissues of the nose and the ligament are compressed over the barbs, holding the ligament into a new position. The excess implant is then cut below the skin surface.

According to another aspect the device is created from dissolvable material such as polydiaxanone (PDO) or polylactic acid (PLA), but is not limited to these and other embodiments may be non-dissolvable material such as nylon or other such material. The central implant may be malleable, rigid, or flexible.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Turn now to the drawings, which accompany the following detailed description and illustrate various aspects, embodiments, features, and elements of the claimed inventions and the context for the use thereof. While exemplary embodiments and aspects are described herein, it will be understood that various modifications to the methods and devices can be made without departing from the scope of the present invention, which are solely limited by the appended claims. For example, the size, shape, position, angles, materials, and other aspects of the implant and barb may vary from those illustrated. Furthermore, the sequential recitation of steps in any claim is not a requirement that the steps be performed in any particular order, unless otherwise so stated.

The following is a description of certain non-limiting preferred embodiments and/or aspects of the claimed invention. Those skilled in the art will recognize, or be able to ascertain using no more than routine experimentation, many equivalents to the specific embodiments and/or aspects of the invention described herein. Those of ordinary skill in the art will appreciate that various changes and modifications to this description may be made without departing from the spirit or scope of the present invention, as defined in the claims that are appended following this description.

Figure 1A:
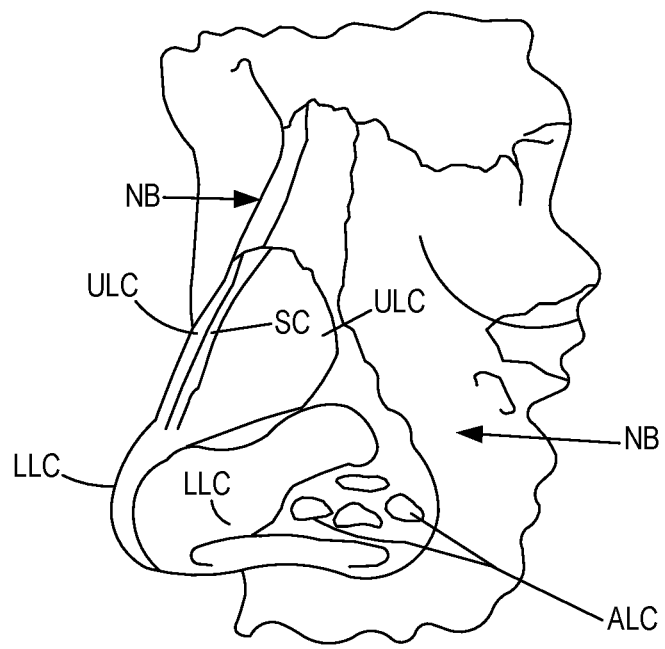
FIG. 1, consisting of FIGS. 1A and 1B, is a perspective view of the front, top and left sides of an exemplary patient's nose including skeletal components and cartilage, and a bottom, upwardly looking view of the components of the exemplary patient's nose, respectively.

Turning now to the drawings, in which like numerals indicate like elements or components or structure or context throughout the several views, FIG. 1A is a perspective view of the front, top and left sides of an exemplary patient's nose including skeletal components and cartilage. Labeled are the nasal bone (NB), upper-lateral cartilage (ULC), lower-lateral cartilages (LLC) and septal cartilages (SC), as well as accessory lateral cartilage (ALC).

Figure 1B:
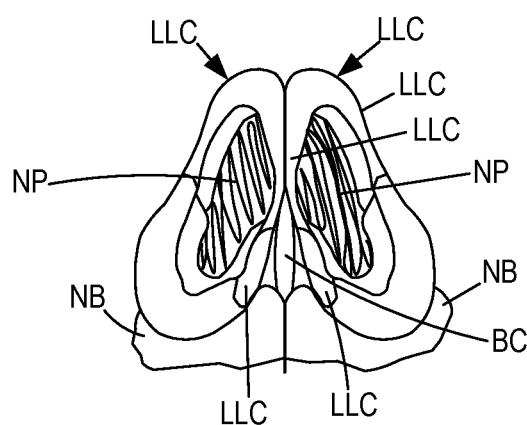

FIG. 1B is a bottom, upwardly looking view of the components of the exemplary patient's nose, showing the entry into the patient's nostrils or nasal passages (NP).

Figure 2A:
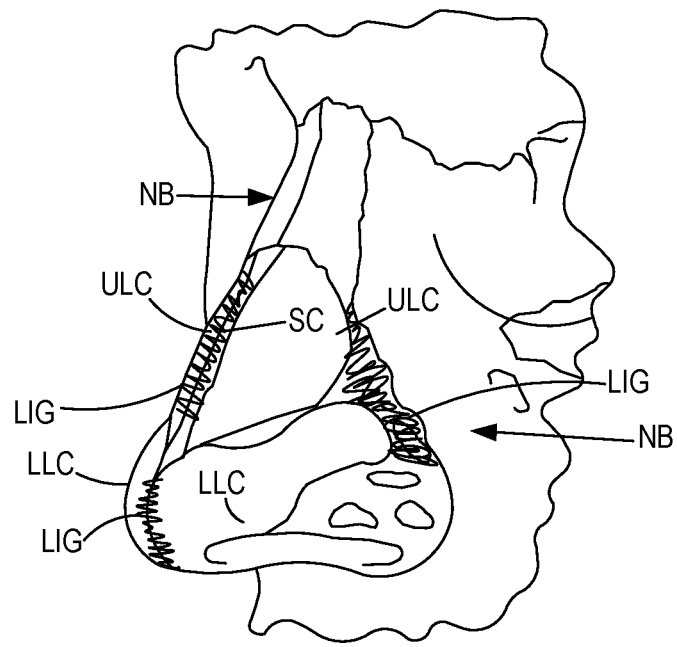
FIG. 2, consisting of FIGS. 2A and 2B, is a perspective view of the front, top and left sides of an exemplary patient's nose including skeletal components and cartilage, and further illustrating ligaments between cartilage structures from FIGS. 1 and 2 critical to support of the nose, and a bottom, upwardly looking view of the components of the exemplary patient's nose, further illustrating ligaments of the nose, respectively.

FIG. 2A is a perspective view of the front, top and left sides of an exemplary patient's nose including skeletal components and cartilage, and further illustrating ligaments (LIG) between cartilage structures from FIGS. 1A and 1B critical to support of the nose. These ligaments (LIG) represent the primary targets of the current invention. Of the various components of a patient's nose, the term "nasal connective tissue" (NCT) will be used herein to include upper-lateral cartilage (ULC), lower-lateral cartilages (LLC), septal cartilages (SC), accessory lateral cartilage (ALC), and ligaments (LIG). Although the ligaments (LIG) between cartilage structures may be considered a primary target for application of aspects of the present invention(s), any of these types of NCT are potential target tissue types for application of the disclosed implant, as will be described, and methods for deploying such an implant for the purposes described herein.

Figure 2B:
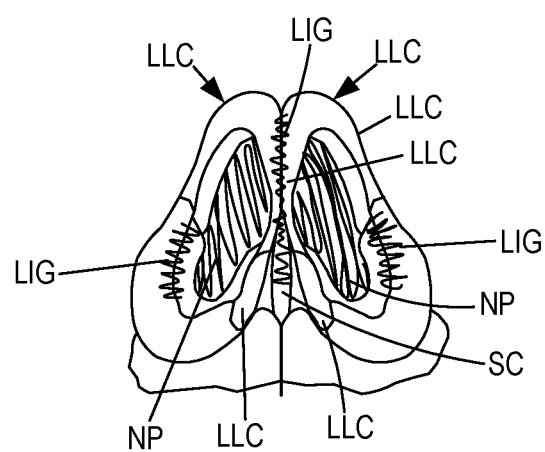

FIG. 2B is a bottom, upwardly looking view of the components of the exemplary patient's nose, further illustrating ligaments (LIG) of the nose.

Figure 3:
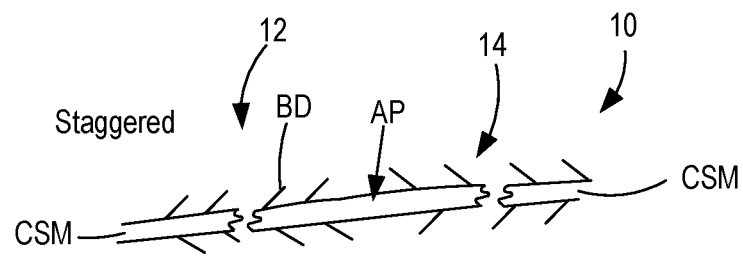
FIG. 3 illustrates an exemplary staggered embodiment of a barbed implant according to aspects of the invention.

FIG. 3 illustrates a barbed implant 10 according to an exemplary staggered embodiment according to aspects of the invention.

Figure 4:
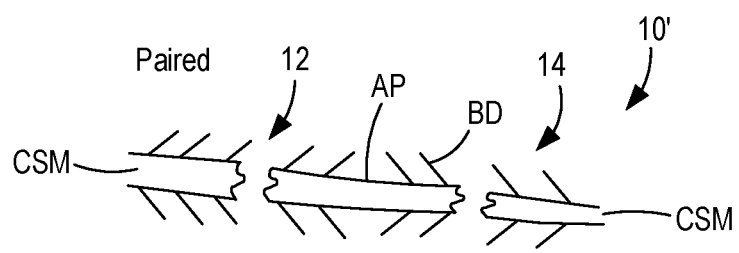
FIG. 4 illustrates an exemplary paired embodiment of a barbed implant according to aspects of the invention.

FIG. 4 illustrates a barbed implant 10' according to an exemplary paired embodiment according to aspects of the invention.

Both implants 10 and 10' include a plurality of spaced-apart, angled barbs (BD), central support material (CSM), and at least one anchor point (AP). Preferably, the implant is made from polydioxanone or other similar dissolvable material. Suitable materials include those typically used as surgical sutures, generally classified as either absorbable or non-absorbable depending on whether the body will naturally degrade and absorb the suture material over time. Absorbable suture materials suitable for use may also include synthetics such as polyglycolic acid, polylactic acid, and caprolactone. Further details of the manner of making the disclosed implants are provided below.

The anchor point AP is a central location of a longitudinally extending material that forms the central support member CSM. The central support member CSM is a generally cylindrical or tubular linear member that supports a plurality of barbs BD. The barbs BD are positioned on opposite sides of the central support member, such that barbs are angled inwardly toward the anchor point AP and positioned on opposite lateral sides of the central support member.

Both embodiments 10 and 10' include a first region 12 with an array of barbs BD to one side of the anchor point AP and a second region 14 with another array of barbs to the opposite side of the anchor point AP. More than one anchor point may be provided on an implant, with arrays of oppositely disposed barbs on either side of such multiple anchor points. Such an embodiment provides for multiple attachment points within the tissue, and more flexibility and options in positioning of the implant.

In the staggered version 10 of FIG. 3, the barbs BD are positioned on opposite sides or surfaces in a staggered configuration, namely, a first or reference barb on one side of the central support member does not have an oppositely disposed second barb on the other side of the central support member, but rather has second and/or third barbs on the other side of the central support member positioned closer to the anchor point and further away from the anchor point that the respective first barb.

In the paired version 10' of FIG. 4, the barbs BD are positioned on opposite sides or surfaces in a paired configuration, namely, a first or reference barb on one side of the central support member has an oppositely disposed second barb on the other side of the central support member, such that pairs of barbs extend in spaced apart pairs along the length of the central support member, disposed on opposite sides of the central support member.

In one aspect, the barbs BD extend in a linear array or line from the anchor point, out to the distal end of the central support member. The barbs BD may terminate a predetermined distance from the distal end of the central support member, or may extend to the distal end.

FIGS. 5-10 illustrates an exemplary insertion technique or method according to aspects of the invention. In these figures, stages labeled LLC represent lower lateral cartilage, SSL represents structural support ligaments, PB represents bone of the piriform nasal aperture, BD represents barbs, SK represents skin of the nasal vestibule or external nose, and LNA and RNA represent left and right nasal apertures, respectively.

Figure 5:
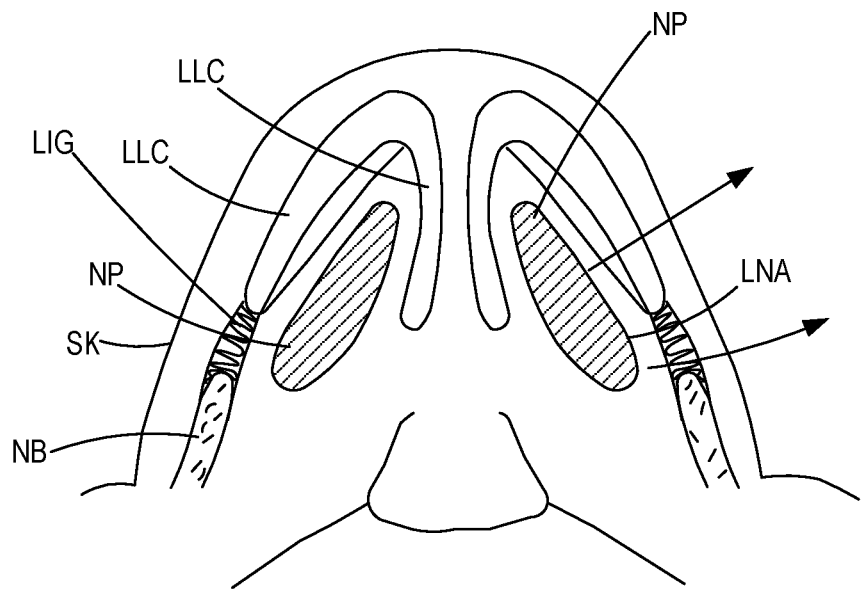
FIGS. 5-10 illustrate steps of an insertion technique or method for placement of a barbed implant according to aspects of this disclosure.

In FIG. 5, the patient's nostrils are accessed for placement of an implant 10, not shown. The left nasal aperture is shown as LNA, and the right nasal aperture is shown as RNA.

Figure 6:
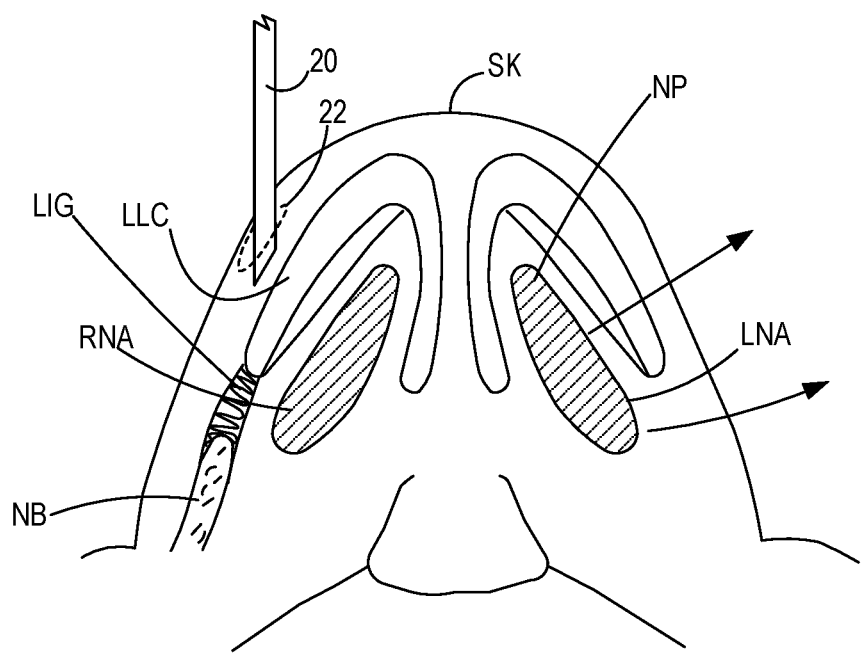

In FIG. 6, a hypodermic needle 20 is inserted through the skin SK of the nose through the lower lateral cartilage LLC to form a pilot hole 22 for insertion of an implant 10, not shown. The pilot hole 22 extends inwardly through the lower lateral cartilage LLC along the lining of the nasal passage toward the nasal bone, parallel to the surface of the bone.

Figure 7:
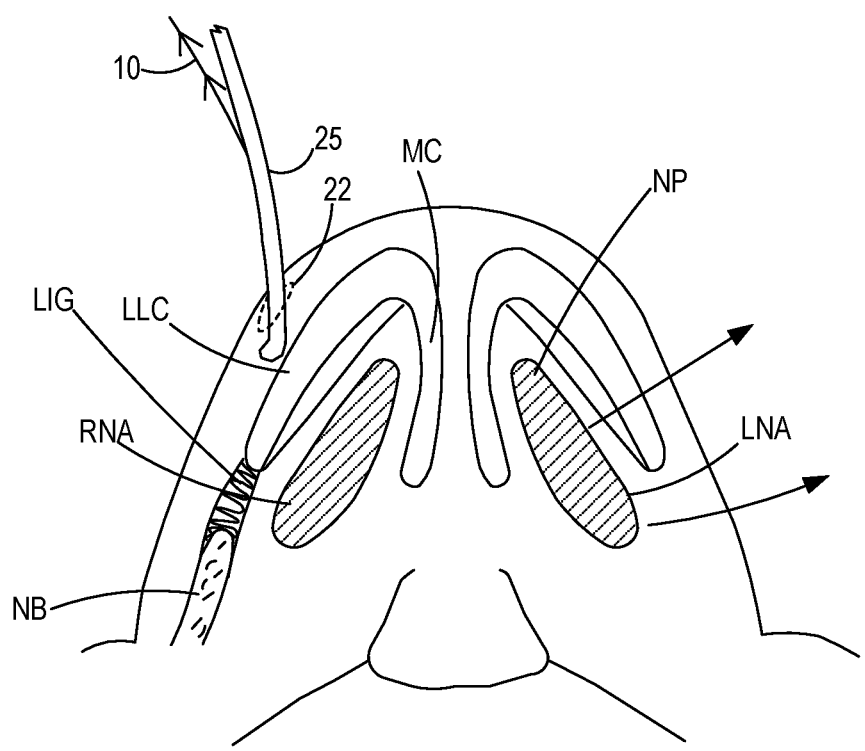

In FIG. 7, a tunneling device 25 is inserted into the pilot hole 22, to provide a portal or sheath for insertion of a barbed implant 10. Preferably, the tunneling device 25 is a tubular element having a blunt end or a sharp tipped end.

Figure 8:
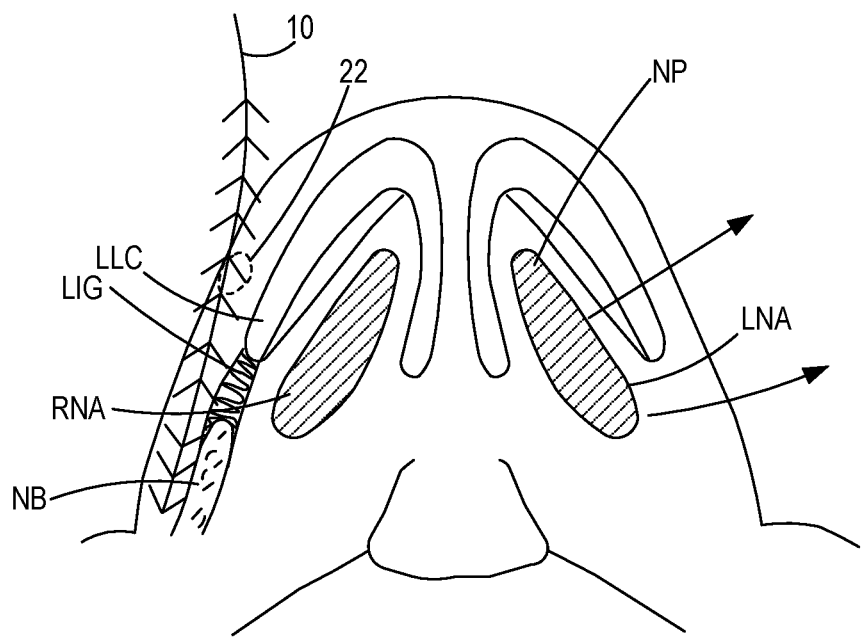

In FIG. 8, the barbed implant 10, whether paired or staggered, is initially inserted through the tunneling device 25 (not shown) into the pilot hole 22, to engage with the ligament LIG extending alongside the nasal passage. Preferably, the implant 10 terminates adjacent to the nasal bone NB, or spaced apart from the nasal bone a predetermined distance.

Figure 9:
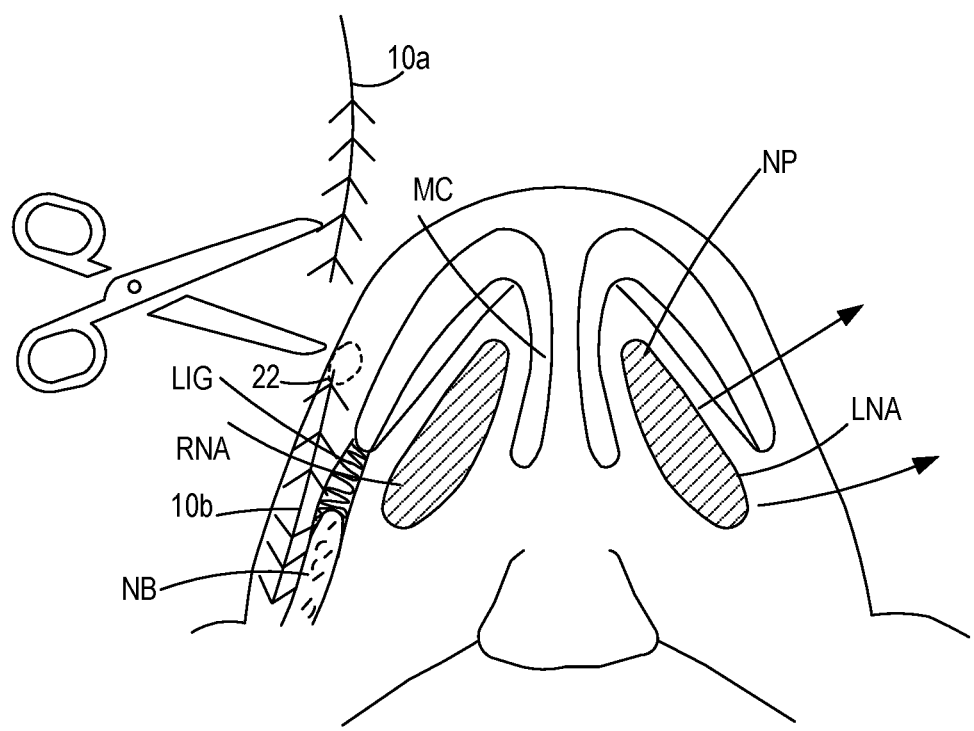

In FIG. 9, pressure is applied to the barbed implant 10 while compressing the ligament and holding the implant stable, while moving the tissues over the implant to a desired position. As shown in the figure, this biases the tissue of the nasal passage outwardly to expand the nasal aperture, e.g. the right nasal aperture RNA as shown in this figure. Any portion of the barbed implant 10a that remains outside the pilot hole 22 is cut with scissors or the like, leaving a portion 10b embedded in the tissue.

Figure 10:
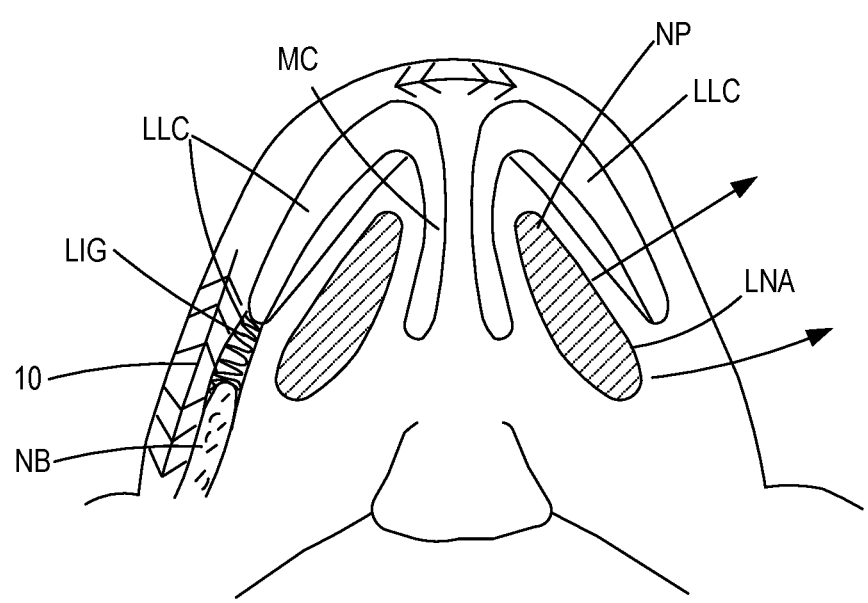

In FIG. 10, the implant 10 is shown in place, with excess material trimmed. In the final position, the implant 10 compresses the ligament and biases the lower lateral cartilage LLC toward the nasal bone NB, thereby expanding the nasal aperture, the right nasal aperture RNA in this example.

According to an aspect of this disclosure, the implant can be removed percutaneously by a small incision and the use of a hook such as a phlebotomy hook. Removal at the time of the insertion can be accomplished by simply holding the tissue stable and applying traction or pulling on the implant prior to final training of the implant. Implants which have been in place for an extended period of time can have radio frequency (RF) therapy applied for accelerated degradation of the implant, e.g. when the implant is composed of polydioxanone or other similar dissolvable material.

FIGS. 11-12 are partial cross-sectional views of tissue showing steps of a method according to an aspect of this disclosure.

Figure 11A:
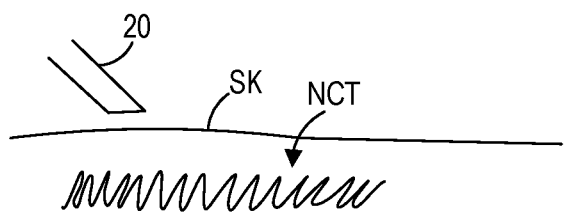
FIG. 11, consisting of FIG. 11A-11G, are partial cross-sectional views of tissue showing steps of a method according to an aspect of this disclosure, with FIGS. 11F and 11G showing plicated and compressed connective tissue resulting from application of aspects of a disclosed method.

In FIG. 11A, exemplary nasal connective tissue (NCT) is shown in cross section, with a hypodermic needle 20 shown prepositioned above the skin SK and proximate to the tissue in anticipation of insertion to form a pilot hole. The nasal connective tissue (NCT) is to be shortened and/or compressed and/or otherwise reshaped or modified so as to provide the benefits of the invention.

Figure 11B:
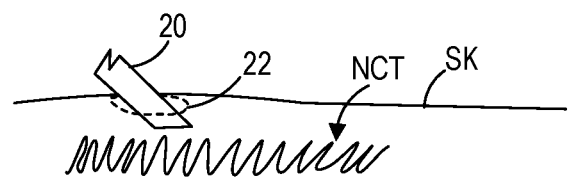

In FIG. 11B, the hypodermic needle 20 is shown inserted into the nasal connective tissue, thereby creating a pilot hole 22.

Figure 11C:
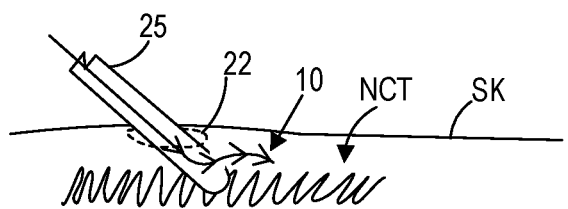

In FIG. 11C, a tunneling device 25 is shown inserted into the pilot hole 22, after removal of the needle 20 in FIG. 11B. The tunneling device 25 is preferably a blunt, or may be a sharp tipped, tubular device that allows dissection and placement by insertion of the disclosed implant 10.

Figure 11D:
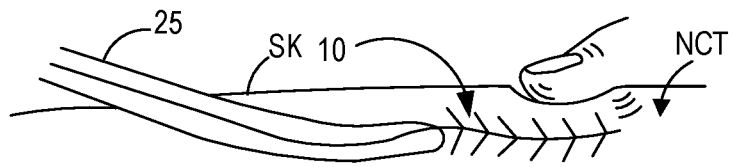

FIG. 11D illustrates removal of the tunneling device 25 from the tissue NCT, leaving behind the implant 10. As the tunneling device 25 is removed, pressure/compression is applied, such as by finger pressure to the skin and tissue. The application of pressure allows the distal end of the implant 10 to engage within the tissue and remain, as the tunneling device is withdrawn.

Figure 11E:
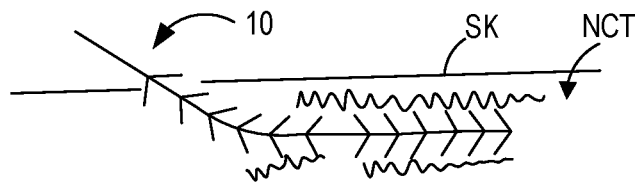

FIG. 11E illustrates the tissue NCT after removal of the tunneling device, leaving a portion of the implant 10 exposed above the skin.

Figure 11F:
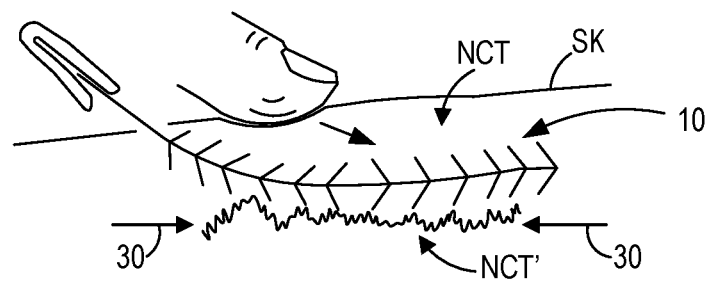

In FIG. 11F, the exposed portion of the implant 10 is clamped or held with a holding device, while pressure is applied by a finger to cause the barbs of the implant to embed in the tissue. As can be seen in FIG. 11F, the ligament and connective tissue NCT may be compressed or shortened, as suggested by arrows 30, resulting in plicated or pleated tissue NCT'.

Figure 11G:
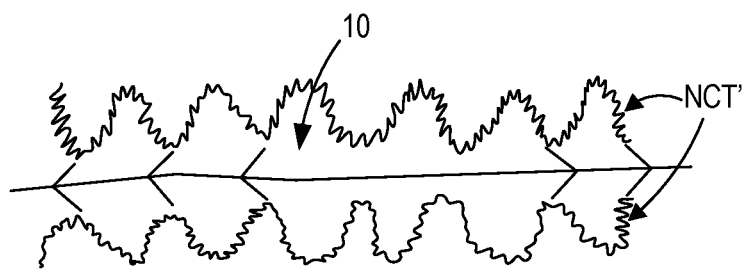
Figure 12A:
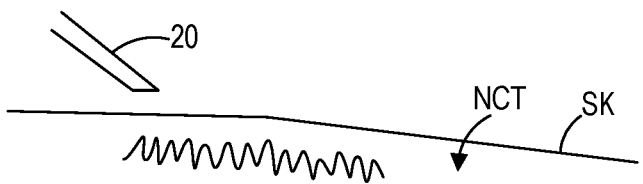
FIG. 12, consisting of FIG. 12A-12G, illustrate steps of an insertion technique or method for placement of a barbed implant according to other aspects of this disclosure.
Figure 12B:
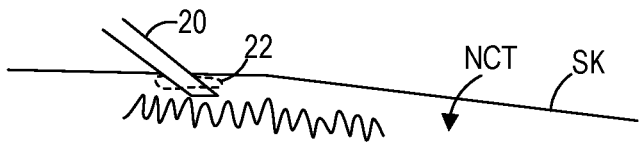
Figure 12C:
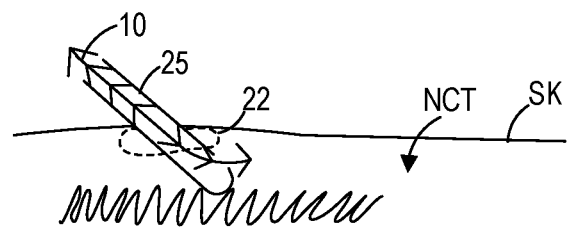
Figure 12D:
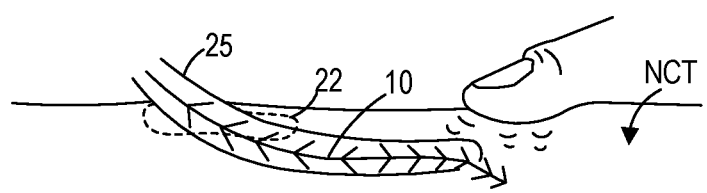
Figure 12E:
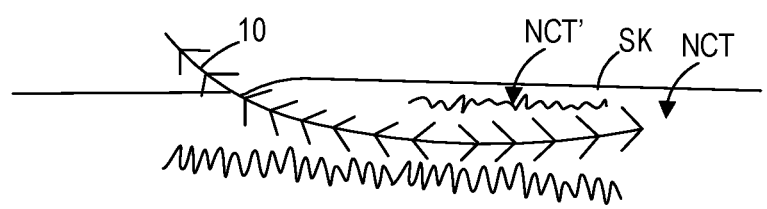
Figure 12F:
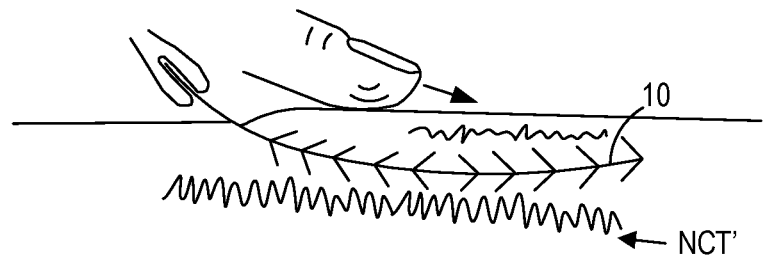
Figure 12G:
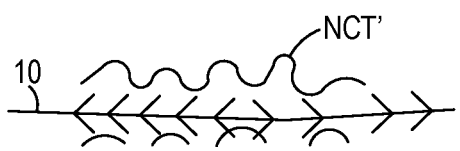

FIG. 11G is a partial cross-sectional view of nasal connecting tissue NCT showing a barbed implant 10 according to this disclosure embedded in the tissue and showing plicated and compressed or shortened connective tissue NCT' resulting from application of aspects of the disclosed method. It will be appreciated that the plicated tissue NCT' resulting from application of the disclosed method(s) provides for an increased air flow through the nasal passages, and can also result in a change in the patient's appearance, in that the nostrils may be made to appear fuller or larger, thereby enhancing the cosmetic appearance.

FIG. 12, consisting of FIGS. 12A-12G, illustrate steps of an insertion technique or method for placement of a barbed implant according to other aspects of this disclosure.

FIGS. 12A through 12G are similar to those shown above in FIGS. 11A through 11G, but show in more detail the manner in which the nasal connective tissue NCT is compressed over the implant 10 as a result of applying pressure to the skin while positioning the implant and moving the implant once embedded in the tissue to plicate the tissue, thereby compressing the tissue over the implant, forming the plicated tissue NCT'.

From the foregoing, it will be appreciated from the foregoing that expansion of the nasal aperture by treatment of the nasal ligaments is achieved nonsurgically by a minimally invasive technique according to aspects of the invention. Treatment of the nasal ligaments includes injecting a barbed working implant into the tissues of the nasal ligament. This effects tightening by compressing the ligament between oppositely oriented barbs on the implant and by employing a material which, in one aspect, gradually dissolves and is replaced by elastic and fibrous tissues resulting from the inflammatory response. The implant can be utilized to strengthen the ligaments between the lower and upper lateral cartilages and the surrounding nasal bones. The implant can also be used to strengthen the attachments of ligaments between the right and left upper and lower lateral cartilages across the midline. Further, the lower lateral cartilages are attached to the cartilage portion of the nasal septum and this ligament can be strengthened with the implant thus allowing for tightening of the lateral nasal wall along a third vector. Finally, application of this method and device along the ligament between the upper lateral cartilages and septum and nasal bones helps lift cartilage and soft tissue out of the airway.

Preferably, the disclosed implant 10 is fabricated from a biodegradable material such as polydiaxanone (abbreviated PDO) with barbs attached to and angled more or less acutely away from the central suture material which comprises a continuous thread or cord-like structure. The barbs can be paired or staggered, as described above. The orientation of the barbs is such that an anchor point (such as the midpoint of the suture material or another advantageous position along the central suture) is surrounded with oppositely oriented barbs. There may be more than one anchor point but the wider aspect of the paired or staggered barbs is closer to the "anchor point" than the more narrow attachment to the central suture continuous thread. The barbs are preferably of sufficient stiffness and length to dig into and retain the surrounding soft tissue of the nasal ligaments. The barbs can be created by any variety of manufacturing techniques such as molding barbs onto the suture material of the continuous thread. In another embodiment, the barbs can be created cutting the central thread to achieve the desired barbs.

According to another aspect, the barbed implant material is placed utilizing a blunt tipped hollow needle similar to a hypodermic needle placed though a pilot hole created in the skin by a narrow cutting device such as a large gauge hypodermic needle or narrow tipped scalpel. The method further comprises steps of placing the implant across the desired ligament and detaching it from the delivery device with a portion of the barbed implant extending beyond the skin. The implant is then grasped to provide counter tension as the soft tissues of the nose and the ligament are compressed over the barbs, holding the ligament into a new position. The excess implant is then cut below the skin surface. According to another aspect the device is created from dissolvable material such as polydiaxanone (PDO) or polylactic acid (PLA), but is not limited to these and other embodiments may be non-dissolvable material such as nylon or other such material. The central implant may be malleable, rigid, or flexible.

In the claims, articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that embodiments of the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, embodiments of the invention encompass compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

What is claimed is:

1. A method for expanding a nasal passage of a patient to facilitate nasal breathing and air flow, comprising the steps of:
providing an implant comprising a support material forming an elongate central support member having a plurality of spaced-apart, angled barbs positioned along a surface of the central support member along a length of the central support member, on either side of an anchor point of the central support member;
inserting a needle through a lower lateral cartilage of the patient to form a pilot hole for insertion of the implant, the pilot hole extending inwardly through the lower lateral cartilage along a lining of the nasal passage toward a nasal bone;
inserting a tunneling device into the pilot hole to provide a portal or sheath for insertion of the implant;
introducing the implant through the tunneling device into the pilot hole to engage with a ligament extending alongside the nasal passage;
terminating insertion of the implant adjacent to the nasal bone of the patient or spaced apart from the nasal bone a predetermined distance; and
applying pressure to the implant while compressing the ligament so as to engage and retain the ligament against the barbs and bias the lower lateral cartilage outwardly to expand the nasal passage.

2. The method of claim 1, further comprising the step of removing any portion of the implant that remains outside the pilot hole with scissors or the like.

3. The method of claim 1, wherein the central support member comprises a generally cylindrical linear member that supports the plurality of barbs on opposite sides of the central support member, such that barbs are angled inwardly toward the anchor point and positioned on opposite lateral sides of the central support member.

4. The method of claim 1, wherein the central support member comprises a generally cylindrical linear member that supports the plurality of barbs on opposite sides of the central support member, such that barbs are angled inwardly toward the anchor point and positioned on opposite lateral sides of the central support member; and
wherein the central support member comprises a first region to one side of the anchor point and a second region to the opposite side of the anchor point, where the barbs are angled with a hypotenuse extending from an apex on the surface of the central support member upwardly and away from the surface of the central support member toward the anchor point.

5. The method of claim 1, wherein the plurality of barbs are positioned on opposite sides or surfaces in a staggered configuration such that a first or reference barb of the plurality of barbs on one side of the central support member does not have an oppositely disposed second barb on the other side of the central support member.

6. The method of claim 1, wherein the plurality of barbs are in a paired configuration such that the barbs are positioned on opposite sides or surfaces, with a first or reference barb of the plurality of barbs on one side of the central support material has an oppositely disposed second barb of the plurality of barbs on the other side of the central support material, such that pairs of barbs extend in spaced apart pairs along the length of the central support member, disposed on opposite sides of the central support member.

7. The method of claim 1, wherein the barbs extend in a linear array or line from the anchor point, out to a distal end of the central support member.

8. The method of claim 7, wherein the barbs terminate a predetermined distance from the distal end of the central support member, or may extend to the distal end.

9. The method of claim 1, wherein the support material of the implant comprises a dissolvable material such as polydiaxanone (PDO) or polylactic acid (PLA).

10. The method of claim 1, wherein the support material of the implant comprises a non-dissolvable material such as nylon or other such material.

11. The method of claim 1, wherein the implant is selected to be either malleable, rigid, or flexible.

* * * * *